United States Patent [19]
Slagboom

[11] Patent Number: 5,885,247
[45] Date of Patent: Mar. 23, 1999

[54] RADIAL GUIDING CATHETER CURVE

[75] Inventor: Teunis Slagboom, Bussum, Netherlands

[73] Assignee: Medtronic, Inc., Minneapolis, Minn.

[21] Appl. No.: 928,819

[22] Filed: Sep. 12, 1997

[51] Int. Cl.$^6$ .................................................. A61M 37/00
[52] U.S. Cl. ........................... 604/95; 604/264; 604/200; 604/201
[58] Field of Search ............................. 604/45, 200, 202, 604/264

[56] References Cited

U.S. PATENT DOCUMENTS

| | | | |
|---|---|---|---|
| 4,822,345 | 4/1989 | Danforth | 604/282 |
| 5,045,072 | 9/1991 | Castillo et al. | 604/280 |
| 5,203,776 | 4/1993 | Durfee | 604/264 |
| 5,603,704 | 2/1997 | Brin et al. | 604/281 |

FOREIGN PATENT DOCUMENTS

| | | | |
|---|---|---|---|
| WO9212754 | 8/1992 | European Pat. Off. | A61M 25/100 |
| WO9726038 | 7/1997 | European Pat. Off. | A61M 25/00 |
| 0728494 | 8/1996 | Netherlands | A61M 25/00 |

OTHER PUBLICATIONS

Mallinckrodt Diagnostic Catheter.—1990.
Imoger Angiographic Catheter—Meditech.
Roubin, Cook Cardiology, LuMax™ Flex Guiding Catheters.
Pfizer Schneider, Kimny™ Radial.
Medtronic UC9001552aEN, © 1991, Short Amplatz Type Left Curves, Amplatz Type Left Curves.
Application Ser. No. 08/543,992, Copend, Brin et al., filing date, Oct. 17, 1995.

*Primary Examiner*—John D. Yasko
*Assistant Examiner*—N. Kent Gring
*Attorney, Agent, or Firm*—Dianne Plunkett Latham; Harold R. Patton

[57] ABSTRACT

A radial guiding catheter comprising a first straight leg connected to a first curve. The first curve has an angle such that the first curve can be disposed just proximal to the coronary ostium. The first curve is connected to a second straight leg. The second straight leg is connected to a second curve such that the second curve can be disposed within the aortic valve. The second curve has a direction opposite the first curve. The second curve is connected to a third straight leg. The distance between the second straight leg and the third straight leg is sufficient to cause the distal end of the first straight leg to engage the left coronary artery. The third straight leg is connected to a third curve, the third curve having a direction opposite the second curve such that the third curve is disposed along the ridge of the brachial artery. The third curve is connected to the forth straight leg such that the catheter provides greater back up support with the contralateral wall of the aorta just distal to the aortic valve.

22 Claims, 3 Drawing Sheets

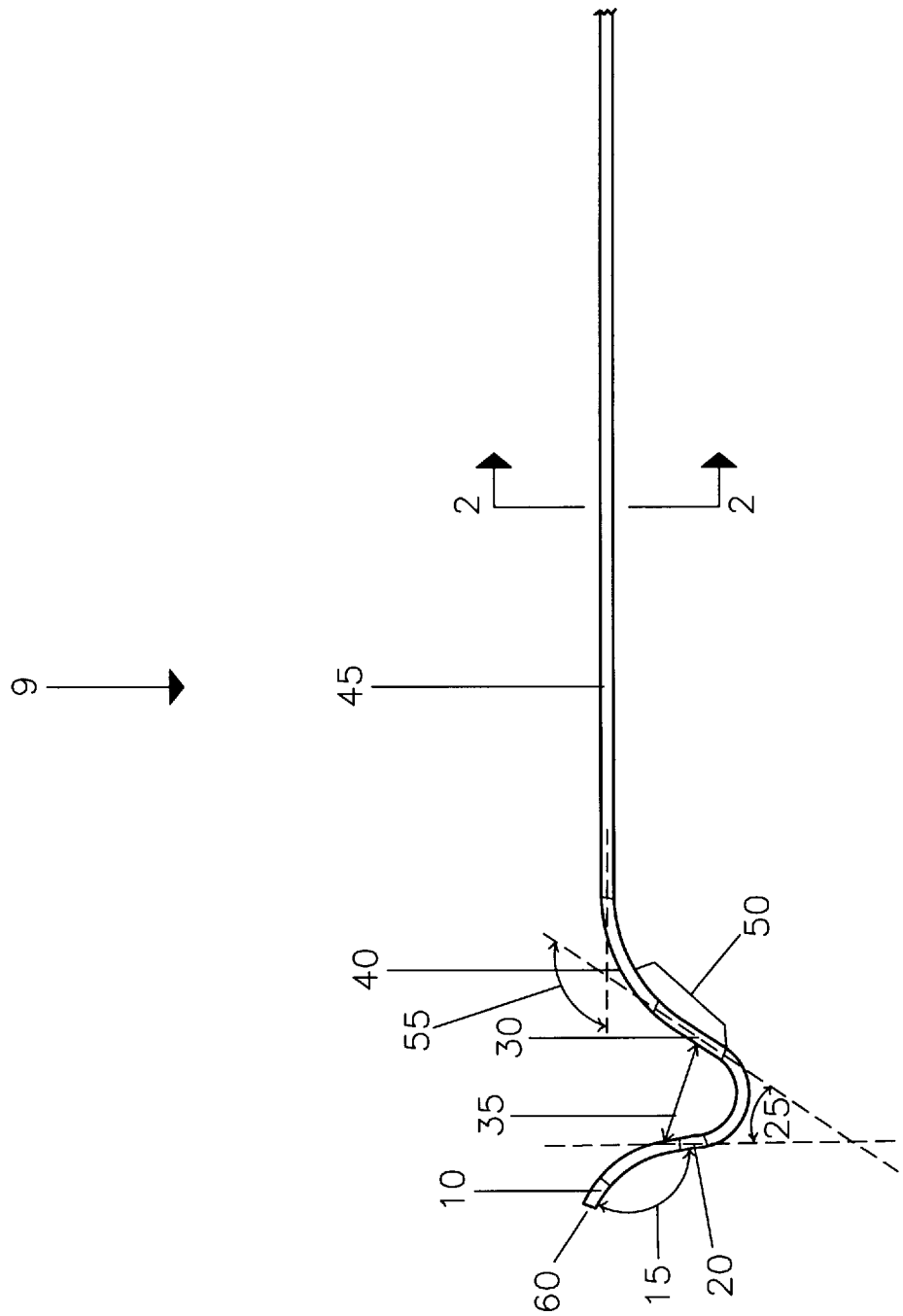

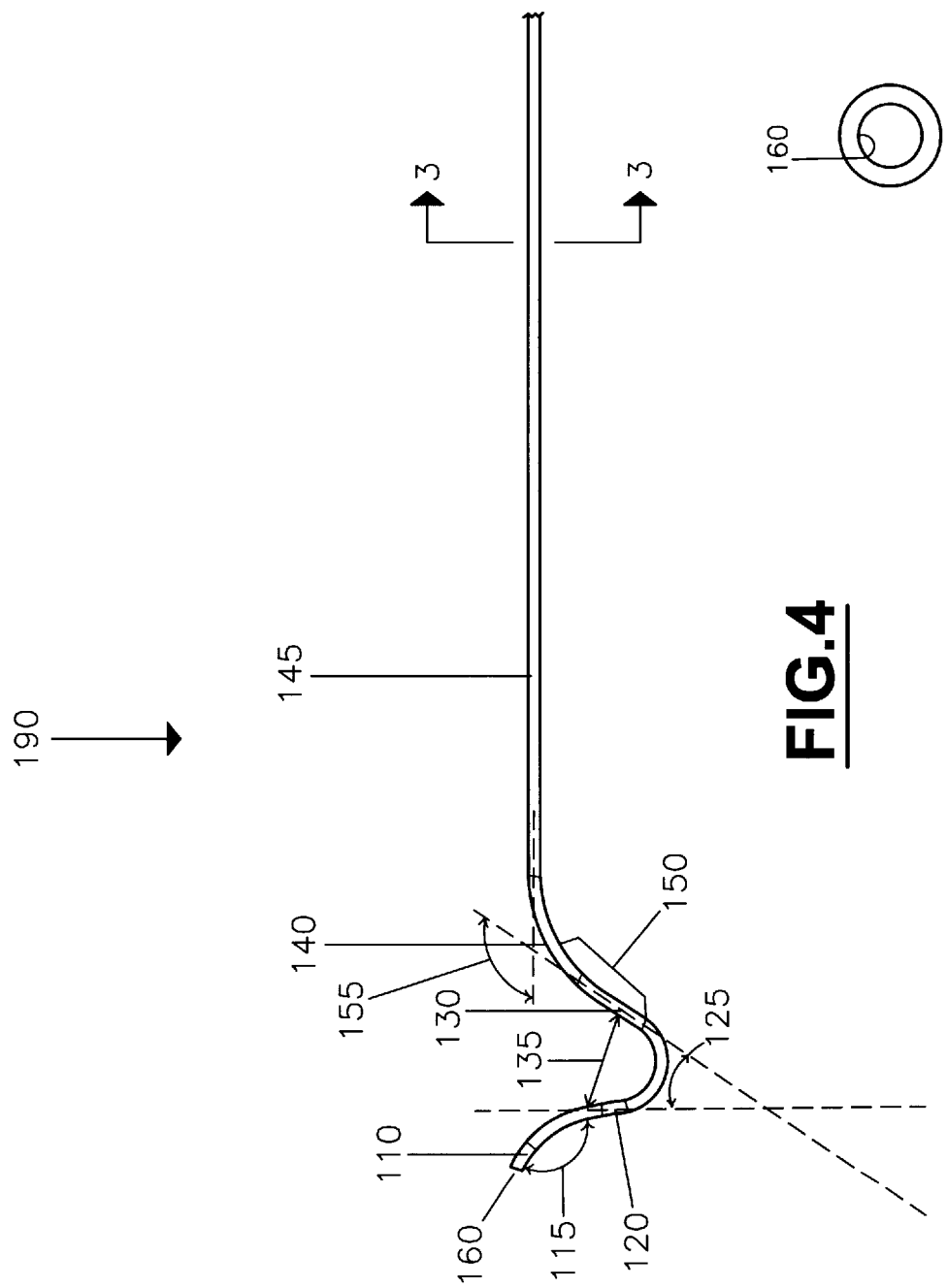

RADIAL GUIDING CATHETER CURVE

FIELD OF THE INVENTION

The present invention relates to guiding catheters, and more particularly, to a guiding catheter with a curve shape suitable for transradial catheterization which provides an improvement in support for interventional devices which are delivered through the lumen of the guiding catheter. Such a guiding catheter can be used in PTCA procedures such as balloon angioplasty, angiography, atherectomy, stent implantation procedures, or radiology procedures.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically, a guidewire is steered through the vascular system to the lesion site of therapeutic interest. A dilatation catheter is inserted over the guidewire and is tracked along the guidewire to the lesion where the catheter is inflated to dilate the lesion. A guiding catheter acts as a support conduit for both the guidewire and the dilatation catheter. The shape of the guiding catheter, and particularly the distal shape, strongly influence the ability of the physician to position the tip of the guiding catheter within the target lesion. Further, the distal shape is influential in providing support for the interventional device as the physician attempts to manipulate the device within the vasculature of the patient.

Many catheters use the femoral artery approach in the patient's leg. The disadvantage of the femoral approach is the length of time the patient is required to remain in the hospital. With the femoral approach, the size of the puncture site will range from 5 French (F) in a diagnostic procedure to 10 F in an angioplasty procedure. The majority of femoral procedures world wide are performed with 7 F or 8 F catheters, while approximately 15% of femoral procedures are performed with 9 F or 10 F catheters. Once the catheter or sheath has been removed from the femoral artery after arterial access, the femoral puncture site bleeding must be stopped. This can be done by manual pressure applied from 10 to 40 minutes, or by a compression assist device which may be used for a similar amount of time. Typically compression will be administered in the catheter laboratory following a diagnostic procedure or in the cardiac care unit or holding area following an angioplasty procedure. With either method, the patient must lie supine for a minimum of four hours, and remain in bed for an additional 16 to 20 hours. The patient must be monitored by hospital support staff during this time.

Because the radial artery is smaller than the femoral artery, a typical size of a radial guiding catheter for angiographic or coronary applications is 6 F. The advantage of a radial artery approach in the wrist is that the wrist puncture wound is smaller than the femoral puncture wound and hemostasis is achieved faster thereby eliminating the patient's overnight stay in the hospital. More rapid hemostasis results in reduced incidence of access-site related major complications.

EP 728,494 to Kiemeneij discloses a radial guiding catheter curve having a distal bridge shaped portion which has a distal arch defining a primary curve which has a concavity oriented towards the proximal end of the bridge. It also has a top defining a secondary curve, the secondary curve having a concavity oriented between the first distal straight portion and the proximal end of the bridge. In addition, it has a proximal arch defining a tertiary curve, the tertiary curve having a concavity oriented towards the first distal straight portion. The proximal arch is connected to a straight shaft. The shaft is stiff and the bridge shaped portion has a flexibility extending at least up to and including the primary curve and a stiffness extending at least up to and including the tertiary curve.

The left Amplatz curve is constructed on variations of a basic shape having a first straight shaft portion followed by a first curve in a first direction followed by a second curve in the opposite direction followed by a second straight shaft portion. Examples of these prior art curves can be found in Medtronic marketing literature UC9001552aEN copyright 1991.

A radial approach necessitates the use of the brachial artery. It is difficult to engage the coronary artery from the brachial artery with the prior art radial curves due to insufficient back-up support. What is needed is a guiding catheter shape better tailored to the anatomy so that the guiding catheter will orient coaxially with the coronary ostium for the interventional device as the device is being manipulated through the vasculature to the target lesion. It is an object of the invention to provide improved back-up support in a radial approach guiding catheter.

SUMMARY OF THE INVENTION

The invention comprises a radial guiding catheter having a first straight leg connected to a first curve. The first curve has an angle such that the first curve can be disposed just proximal to the coronary ostium. The first curve is connected to a second straight leg. The second straight leg is connected to a second curve such that the second curve can be disposed within the aortic valve. The second curve has a direction opposite the first curve. The second curve is connected a third straight leg. The distance between the second straight leg and the third straight leg is sufficient to cause the distal end of the first straight leg to engage the left coronary artery. The third straight leg is connected to a third curve, the third curve having a direction opposite the second curve such that the third curve is disposed along the ridge of the brachial artery. The third curve is connected to the forth straight leg such that the catheter provides greater back up support with the contralateral wall of the aorta just distal to the aortic valve.

BRIEF DESCRIPTION OF THE DRAWINGS

FIG. 1 depicts applicant's radial guiding catheter shape, the SBU 0.75;

FIG. 2 depicts a cross-section of FIG. 1 along the lines 2—2;

FIG. 3 depicts a cross-section of FIG. 4 along the lines 3—3;

FIG. 4 depicts applicant's radial guiding catheter shape, the SBU 1.0; and

DETAILED DESCRIPTION OF THE PREFERRED EMBODIMENTS

Figure 5:
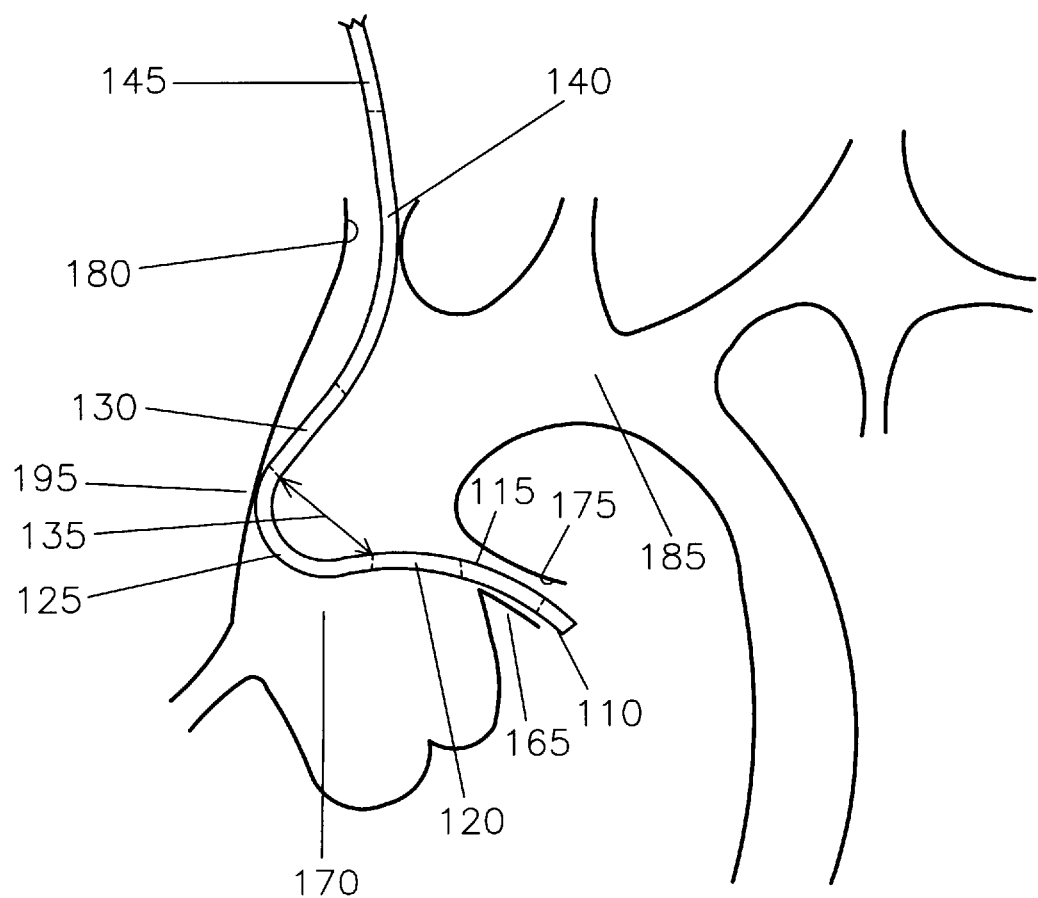
FIG. 5 depicts the SBU 1.0 when placed in the coronary vasculature.

Applicant's invention provides improved back-up support in a radial approach guiding catheter by assuming a buttressing configuration with the contralateral wall of the aorta just distal to the aortic valve so that the guiding catheter will orient coaxially with the coronary ostium. Applicant's guiding catheter has two embodiments, the Slagboom Back-up 0.75 (SBU 0.75) seen in FIG. 1 and the SBU 1.0 seen in FIG. 4. The product designation numbers (0.075, 1.0 etc.) correspond to the Amplatz Left type curves in the prior art available from Medtronic of Minneapolis, Minn. The SBU 0.75 and the SBU 1.0 described in this application are suitable for most patient anatomy sizes. Those skilled in the art would recognize, however that Applicant's invention could be applied to other sizes of Amplatz Left type curves. The choice of a SBU 0.75 over a SBU 1.0 depends on the size of the patient's aortic root and the distance between the patient's aortic valve 170 and the left coronary artery 175.

Applicants' invention, which is shown in FIGS. 1 and 4 comprises a 6 F guiding catheter for angiographic or coronary use at a radial or right brachial artery access site. A standard 6 F guiding catheter such as Applicant's has an outer diameter of 2.0 mm and an inner lumen 60, 160 inner diameter of 0.064 inches.

Applicant's FIG. 1 SBU 0.75 radial guiding catheter 9 comprises a first straight leg 10 at the distal end of the catheter, which is substantially straight and has a length of approximately 4–5 mm. The length of the FIG. 4 SBU 1.0 first straight leg 110 is slightly longer at approximately 6–7 mm. Nine mm was found to be too long for the first straight leg 10, 110 because it too deeply engages the left coronary artery 175. The longer the first straight leg 10, 110 the better the support but the more difficult it is to disengage during guiding catheter 9, 190 withdrawal.

It is advantageous if the first straight leg 10, 110 or a distal portion thereof comprises a softer material. Guiding catheter materials can be chosen from biocompatible, flexible material with a good memory for the original curve in conformity with applicant's co-pending patent Ser. No. 08/543,992 which is hereby incorporated by reference. Soft tips are preferred at the distal end of guiding catheters because they reduce the damage to the coronary ostium 165.

Extending proximally from the first straight leg 10, 110 is a first curve 15, 115 in a first direction at an angle of approximately 120–150 degrees. Extending proximally from the FIG. 1 SBU 0.75 first curve 15 is a second straight leg 20 of approximately 6–7 mm. Extending proximally from the FIG. 4 SBU 1.0 first curve 115 is a second straight leg 120 of approximately 7–8 mm. Extending proximally from the second straight leg 20, 120 is a second curve 25, 125 in the opposite direction of the first curve 15, 115. The second curve 25, 125 has an angle of approximately 20–45 degrees.

Extending proximally from the second curve 25 of the SBU 0.75 is a third straight leg 30 of approximately 20 mm in length. Extending proximally from the second curve 125 of the SBU 1.0 is a third straight leg 130 of approximately 23 mm in length. The distance 35 between the second straight leg 20 and the third straight leg 30 is approximately 20 mm for the RS 0.75. The distance 135 between the second straight leg 120 and the third straight leg 130 is approximately 25 mm for the RS 1.0. A distance of 31 mm for distance 35, 135 was found to be too wide for engaging the left coronary artery 175.

Extending proximally from the third straight leg 30, 130 is a third curve 40, 140 in an opposite direction from the second curve 25, 125. Angle 55, 155 is an optimal angle for access between the brachial artery and the aorta. Angle 55, 155 of the third curve 40, 140 may range between 110 degrees and 150 degrees. It is the addition of the third curve 40, 140 to the Left Amplatz type first curve 15, 115 and the Left Amplatz type second curve 25, 125 that permits a firm back-up support with the contralateral wall 195 of the aorta just distal to the aortic valve 170. Angle 55, 155 increases with the length 50, 150 which is between the midpoint of the third curve 40, 140 and the proximal end of the second curve 25, 125, in conformity with the following table:

| Length from Mid Point Third Curve to Proximal End Second Curve | 6 cm | 7 cm | 8 cm |
|---|---|---|---|
| Third Curve Angle (Degrees) | 110 | 120 | 130 |

Extending proximally from the third curve 40, 140 is a forth straight leg 45, 145 at the proximal end of the catheter. The forth straight leg is approximately 85 cm. in length in conformity with the total length of the guiding catheter, 90, 190.

As seen in FIG. 5 the preferred catheter straight leg 110, 120, 145 lengths and angles 115, 125, 140 are chosen so that, when the catheter is inserted into the vasculature, the proximal portion extends from the radial access site to adjacent the aortic arch of the patient, with the third curve 140 disposed along the ridge of the brachial artery 180, the second curve 125 disposed within the aortic valve 170, the first curve 115 disposed just in front of the coronary ostium 165 and the distal tip engaged in the coronary ostium. Such a design provides greater back up support with the contralateral wall 195 of the aorta 185 just distal to the aortic valve 170.

The preceding embodiments are illustrative of the invention and modifications may be made to these embodiments without departing from the scope and breadth of the invention.

| No. | Component |
|---|---|
| 9 | SBU 0.75 Guiding Catheter |
| 10 | SBU 0.75 First Straight Leg |
| 15 | SBU 0.75 First Curve |
| 20 | SBU 0.75 Second Straight leg |
| 25 | SBU 0.75 Second Curve |
| 30 | SBU 0.75 Third Straight Leg |
| 35 | SBU 0.75 Distance Between Second and Third Straight Legs |
| 40 | SBU 0.75 Third Curve |
| 45 | SBU 0.75 Fourth Straight Leg |
| 50 | SBU 0.75 Length Mid Point 3rd Curve to Proximal End 2nd Curve |
| 55 | SBU 0.75 Third Curve Angle |
| 60 | SBU 0.75 Inner Lumen |
| 110 | SBU 1.0 First Straight Leg |
| 115 | SBU 1.0 First Curve |
| 120 | SBU 1.0 Second Straight leg |
| 125 | SBU 1.0 Second Curve |
| 130 | SBU 1.0 Third Straight Leg |
| 135 | SBU 1.0 Distance Between Second and Third Straight Legs |
| 140 | SBU 1.0 Third Curve |
| 145 | SBU 1.0 Fourth Straight Leg |
| 150 | SBU 1.0 Length Mid Point 3rd Curve to Proximal End 2nd Curve |
| 155 | SBU 1.0 Third Curve Angle |
| 160 | SBU 1.0 Inner Lumen |
| 165 | Coronary Ostium |
| 170 | Aortic Valve |
| 175 | Left Coronary Artery |
| 180 | Brachial Artery |
| 185 | Aorta |
| 190 | SBU 1.0 Guiding Catheter |
| 195 | Contralateral Wall |

What is claimed is:

1. A catheter adapted for placement within the human coronary system, the catheter comprising:

a first straight leg having a distal end engaged in the coronary ostium, a proximal end connected to a distal end of a first curve;

the first curve having a first direction such that the first curve can be disposed just proximal to the coronary ostium, the proximal end of the first curve is connected to a distal end of a second straight leg;

a proximal end of the second straight leg is connected to a distal end of a second curve such that the second curve can be disposed within the aortic valve;

the second curve has a direction opposite the first curve, a proximal end of the second curve is connected to a distal end of a third straight leg;

the distance between the second straight leg and the third straight leg being sufficient for the distal end of the first straight leg to engage the left coronary artery, a proximal end of the third straight leg is connected to a distal end of a third curve;

the third curve having a direction opposite the second curve such that the third curve is disposed along the ridge of the brachial artery; and a proximal end of the third curve is connected to a distal end of a forth straight leg such that the catheter provides greater back up support with the contralateral wall of the aorta just distal to the aortic valve.

2. A catheter according to claim 1 wherein the catheter is a 6 French guiding catheter.

3. A catheter according to claim 1 wherein the first straight leg has a length of less than approximately 9 mm.

4. A catheter according to claim 1 wherein the first curve is at an angle of approximately 120–150 degrees.

5. A catheter according to claim 1 wherein the second straight leg has a length of approximately 6–8 mm.

6. A catheter according to claim 1 wherein the second curve is at an angle of approximately 20–45 degrees.

7. A catheter according to claim 1 wherein the second curve has a radius of curvature of approximately 1 cm or less.

8. A catheter according to claim 1 wherein the third straight leg has a length between approximately 20 mm and 23 mm.

9. A catheter according to claim 1 wherein the distance between the second straight leg and the third straight leg is less than approximately 31 mm.

10. A catheter according to claim 1 wherein the third curve is approximately 110–150 degrees.

11. A catheter adapted for placement within the coronary system of a human patient, the catheter comprising:

a first straight leg having a distal end for engagement in the patient's coronary ostium;

a first curve connected at a distal end of the first curve to a proximal end of the first straight leg, the first curve having a first direction such that when the first straight leg in engaged in the patient's coronary ostium, the first curve can be disposed just proximal to the coronary ostium;

a second curve connected at a distal end of the second curve to a proximal end of the first curve, the second curve having a second direction which is opposite to the first direction of the first curve; the second curve connected to the first curve such that the second curve is disposed within the patient's aortic valve when the first curve is disposed proximate to the patient's coronary ostium;

a third curve connected at a distal end of the third curve to a proximal end of the second curve, the third curve having a direction opposite to the direction of the second curve, the third curve connected to the second curve such that when the first curve is disposed proximate to the patient's coronary ostium and the second curve is disposed within the patient's aortic valve the third curve is disposed along a ridge portion of the patient's brachial artery;

a forth straight leg connected to a proximal end of the third curve;

the first, second and third curves connected such that when the first straight leg is engaged in the patient's coronary ostium and the second straight leg is advanced into the patient, the first curve engages the patient's coronary ostium and the catheter flexes at the second curve to engage the catheter with a contralateral wall of the patient's aorta just distal to the patient's aortic valve.

12. A catheter according to claim 11 wherein the catheter is a 6 French guiding catheter.

13. A catheter according to claim 11 wherein the first straight leg has a length of less than approximately 9 mm.

14. A catheter according to claim 11 wherein the first curve is at an angle of approximately 120–150 degrees.

15. A catheter according to claim 11 wherein the second curve is at an angle of approximately 20–45 degrees.

16. A catheter according to claim 11 wherein the second curve has a radius of curvature of approximately 1 cm or less.

17. A catheter according to claim 11 wherein the third curve is approximately 110–150 degrees.

18. A catheter according to claim 11 wherein the first curve is connected with the second curve by a second straight leg.

19. A catheter according to claim 18 wherein the second straight leg has a length of approximately 6–8 mm.

20. A catheter according to claim 11 wherein the second curve is connected with the third curve by a third straight leg.

21. A catheter according to claim 20 wherein the third straight leg has a length between approximately 20 mm and 23 mm.

22. A catheter adapted for placement within the human coronary system, the catheter comprising:

a first straight leg having a distal end and a proximal end connected to a distal end of a fist curve;

the first curve having a first direction and a proximal end of the first curve connected to a distal end of a second straight leg;

a proximal end of the second straight leg is connected to a distal end of a second curve;

the second curve having a direction opposite the first curve and a proximal end of the second curve connected to a distal end of the third straight leg, wherein a proximal end of the third straight leg is connected to a distal end of a third curve;

the third curve having an angle of about 110 degrees to about 150 degrees in a direction opposite the second curve; and a proximal end of the third curve connected to a distal end of a fourth straight leg.

* * * * *